US00PP24015P3

(12) United States Plant Patent
Werner et al.

(10) Patent No.: US PP24,015 P3
(45) Date of Patent: Nov. 5, 2013

(54) *BUDDLEJA* PLANT NAMED 'ICE CHIP'

(50) Latin Name: *Buddleja*
Varietal Denomination: Ice Chip

(75) Inventors: Dennis J. Werner, Raleigh, NC (US); Layne K. Snelling, Cary, NC (US)

(73) Assignee: North Carolina State Univeristy, Raleigh, NC (US)

( * ) Notice: Subject to any disclaimer, the term of this patent is extended or adjusted under 35 U.S.C. 154(b) by 55 days.

(21) Appl. No.: 13/373,181

(22) Filed: Nov. 7, 2011

(65) Prior Publication Data

US 2013/0055478 P1 Feb. 28, 2013

(30) Foreign Application Priority Data

Aug. 25, 2011 (CA) ..... 11-7361

(51) Int. Cl.
*A01H 5/00* (2006.01)

(52) U.S. Cl.
USPC ..... Plt./242

(58) Field of Classification Search
USPC ..... Plt./242
See application file for complete search history.

(56) References Cited

U.S. PATENT DOCUMENTS

| | | | |
|---|---|---|---|
| PP19,950 | P3 | 4/2009 | Werner et al. |
| PP19,991 | P3 | 5/2009 | Werner et al. |
| PP22,143 | P2 | 9/2011 | Podaras |
| 2013/0055479 | P1 | 2/2013 | Werner et al. |

OTHER PUBLICATIONS

Office Action for U.S. Appl. No. 13/373,183 dated Mar. 19, 2013 (6 pages).

*Primary Examiner* — Susan McCormick Ewoldt
(74) *Attorney, Agent, or Firm* — Michael Best & Friedrich LLP

(57) ABSTRACT

*Buddleja* 'Ice Chip' is a new and distinct variety of butterfly bush. The distinguishing traits of 'Ice Chip' include at last one of dwarf plant size, spreading growth habit, gray-green leaf color, attractive white flowers, male sterility and female structures that are essentially sterile.

4 Drawing Sheets

Latin name of the genus and species: Genus: *Buddleja*. Species: hybrid.

Variety denomination: The inventive cultivar of *Buddleja* disclosed herein has been given the variety denomination 'Ice Chip'.

This application claims the benefit of Canadian Application No. 11-7361 filed Aug. 25, 2011.

BACKGROUND OF THE INVENTION

The present invention relates to a new and distinct variety of *Buddleja* (butterfly bush) grown as an ornamental shrub for home and commercial landscapes. Butterfly bush is typically grown for its attractive, fragrant flowers that are borne throughout the growing season.

The new and distinct variety of butterfly bush resulted from a formal breeding program established by the inventors in Raleigh, N.C., United States. One of the objectives of the breeding program was to develop a dwarf, spreading *Buddleja* with white flowers. 'Ice Chip' was selected at a research station in Jackson Springs, N.C. in 2006 from a population of 357 seedling progeny derived from a hand pollinated cross of 'Blue Chip' (female parent: NCSU cultivar tested as NC2004-9, U.S. Plant Pat. No. 19,991)× NC2002-12 (male parent) made in 2005 in Raleigh, N.C. 'Blue Chip' is a complex hybrid containing 3 different species and one botanical variety of *Buddleja* (*B. davidii, B. davidii* var. *nanhoensis, B. lindleyana*, and *B. globosa*). NC2002-12, the other parent of 'Ice Chip', is a hybrid of 'White Ball'× 'Nanho Purple'. 'Nanho Purple' is a variety derived from *Buddleja davidii* var. *nanhoensis*. 'White Ball' is a complex hybrid, presumably containing *B. davidii* and *B. fallowiana*. The pedigree of 'Ice Chip' is shown in Table 1. Of all the parents used in the development of 'Ice Chip', the varieties 'Blue Chip', 'White Ball', 'Nanho Purple', and 'Honeycomb', and the species *Buddleja lindleyana* are available in commerce.

TABLE 1

Pedigree of *Buddleja* 'Ice Chip'.

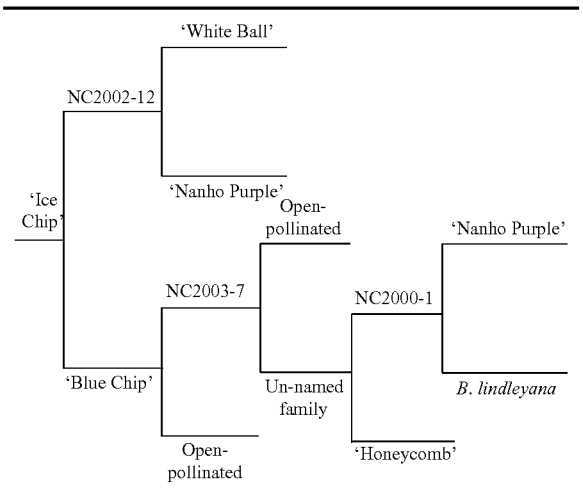

The seeds resulting from the 2005 controlled hybridization process were harvested in fall of 2005 and germinated in a greenhouse in Raleigh, N.C. in the winter of 2006. The resulting 351 seedlings were planted in field trials in spring of 2006 at a research station in Jackson Springs, N.C. These plants flowered in summer 2006, and one plant, designated NC2006-10, was selected for its dwarf plant size, spreading habit, attractive white flowers, and lack of seed set (female sterile). This original plant demonstrated characteristics identical to those subsequently expressed on other plants when propagated from stem cuttings. This single plant is the subject of the present invention *Buddleja* 'Ice Chip'.

The distinguishing traits of 'Ice Chip' include at last one of dwarf plant size, spreading growth habit, gray-green leaf color, attractive white flowers, male sterility and female structures that are essentially sterile. "Essentially sterile" is used because applicants do not preclude the possibility that a seed set may be observed on rare occasions. Ideal cultural conditions for 'Ice Chip' include well-drained soil, full sun, and moderate moisture. 'Ice Chip' exhibits no serious pest or disease problems known to the inventors, except for occasional spider mite infestation during periods of hot, dry weather.

The closest comparison known to the inventors are the varieties 'Blue Chip' (U.S. Plant Pat. No. 19,991), 'White Ball' (non-patented), and 'Podarus 15' (U.S. Plant Pat. No. 22,143). Plants and flowers of this new variety differ from 'Blue Chip'. In direct comparisons of 'Ice Chip' and 'Blue Chip' in the inventor's experimental trials, plants of 'Ice Chip' are consistently more spreading, more highly branched, more dense, and have white flowers, compared to the blue flowers of 'Blue Chip'. 'Ice Chip' is distinctly different from 'White Ball'. In direct comparisons of 'Ice Chip' and 'White Ball' in the inventor's experimental trials, plants of 'Ice Chip' are consistently more spreading as compared to the globose architecture of 'White Ball'. 'Ice Chip' is shorter in height and has greater width as compared to 'White Ball'. In replicated trials of 10 plants of both varieties, two-year-old unpruned plants of 'Ice Chip' attained a height and spread of 48.4 and 125.8 cm, respectively (height/width ratio=0.36), after two years of growth. Plants of 'White Ball' attained a height and spread of 79.7 cm and 100.6 cm (height/width ratio=0.79), respectively. Plants of 'Ice Chip' are different from 'Podarus 15'. In side-by-side comparisons in the inventor's experimental trials, plants of 'Ice Chip' are shorter, have greater branching, and show a denser growth habit as compared to 'Podarus 5' after one full year of growth.

The inventors conducted the first asexual propagation of 'Ice Chip' in fall 2006 in Raleigh, N.C., and 'Ice Chip' has subsequently been propagated in the same location in years 2008, 2009, and 2010. In all cases, the original plant selection was propagated asexually by softwood to semi-hardwood stem cuttings. Such cuttings root readily under mist in about 14 to 21 days, and resume normal growth. Ten plants derived from stem cuttings of the variety were established in experimental test plots in Jackson Springs, N.C. in 2007. During all asexual propagation, the characteristics of the original plant have been maintained. Plants derived from stem cuttings exhibit characteristics identical to those of the original plant, and no aberrant phenotypes have appeared.

Test plantings and performance evaluation over six years at a research station in Jackson Springs, N.C. demonstrate this variety to be relatively consistent in its characteristics even under the different growing conditions associated with yearly climatic variation.

Plants of the new variety are very dwarf after establishment in the field, being less vigorous and more dwarf than most varieties of butterfly bush in commerce. Young plants have averaged about 24.2 cm of height growth per year. Plants are spreading in growth habit. Flowering occurs in the first year of growth on newly formed wood. The inflorescence is a panicle, and shows a white flower color. Flowering usually begins in early June in Jackson Springs, N.C., and continues throughout the growing season until the first freeze event in October or November. An individual inflorescence flowers for about 7-10 days, depending on temperature, but new flowers are made during the entire growing season. The new variety produce no functional male flower parts, and hence makes no pollen. Female fertility of flowers is considered to be essentially sterile, as the new variety sets virtually no seed in a field or landscape setting, an asset in landscape plantings.

'Ice Chip' is distinguished from other related known varieties based on the unique combination of traits including dwarf growth, spreading habit, white flowers, male sterility, and female structures that are essentially sterile.

The new variety has been named the 'ICE CHIP' cultivar. First public offer for sale of 'Ice Chip' was made in Grand Haven, Mich., U.S.A. on Aug. 1, 2011.

SUMMARY OF THE INVENTION

'Ice Chip' is a new and distinct cultivar of butterfly bush that has the following unique combination of desirable features outstanding in a new variety. In combination these traits set 'Ice Chip' apart from all other existing varieties of butterfly bush known to the inventors.

1. 'ICE CHIP' has low vigor resulting in dwarf growth.
2. 'ICE CHIP' demonstrates a dense, spreading growth habit.
3. 'ICE CHIP' exhibits male sterility and female structures that are essentially sterile, having very low seed set, thereby resulting in less opportunity for seedlings to originate in the landscape setting.
4. 'ICE CHIP' has white flower color.

BRIEF DESCRIPTION OF THE DRAWINGS

The photographs in the drawings were made using digital photography techniques, and show the colors as true as reasonably possible by digital photography. Colors in the photographs may differ slightly from the color values cited in the detailed botanical description, which accurately describe the colors of the new *Buddleja* variety 'Ice Chip'. Photographs were taken from two to four-year-old plants growing in Jackson Springs, N.C., except for FIG. 4, which was taken in a greenhouse in Raleigh, N.C.

DETAILED BOTANICAL DESCRIPTION OF THE VARIETY

Figure 1:
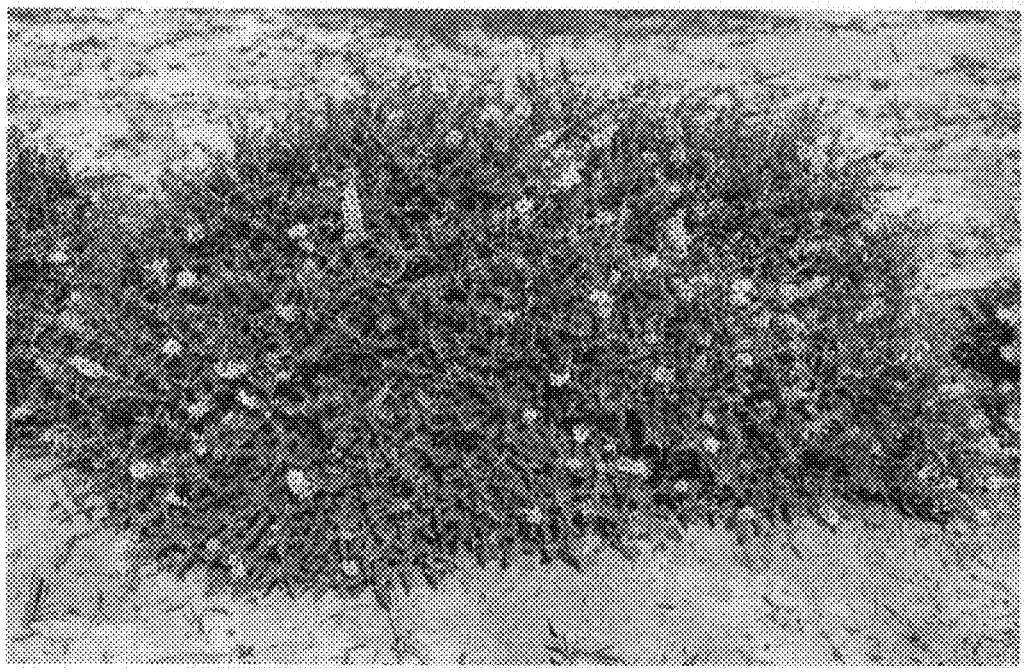
FIG. 1 shows a typical plant of 'ICE CHIP', showing the dwarf growth, spreading growth habit, dense foliage, and white flowers.
Figure 2:
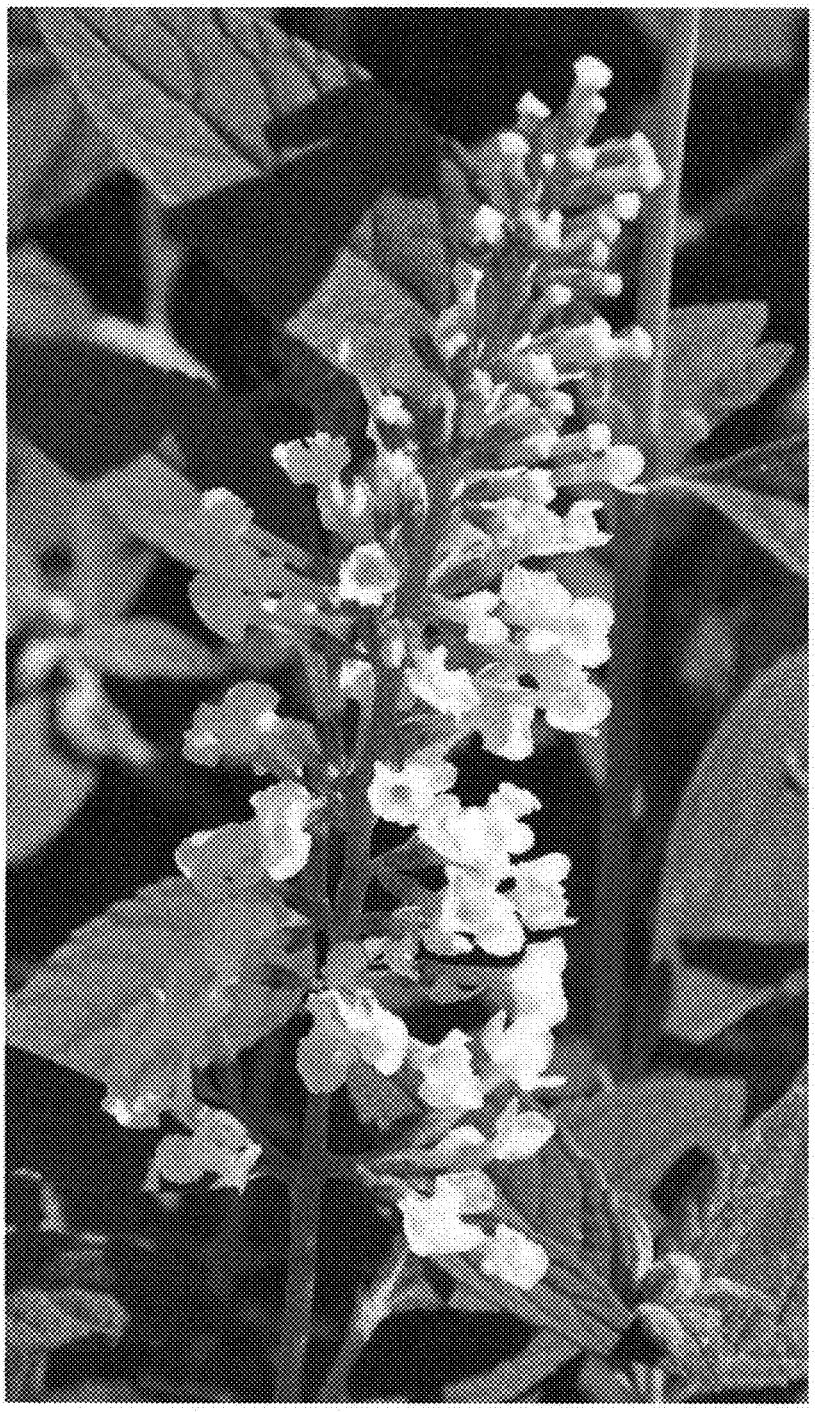
FIG. 2 shows the entire inflorescence of 'ICE CHIP'.
Figure 3:
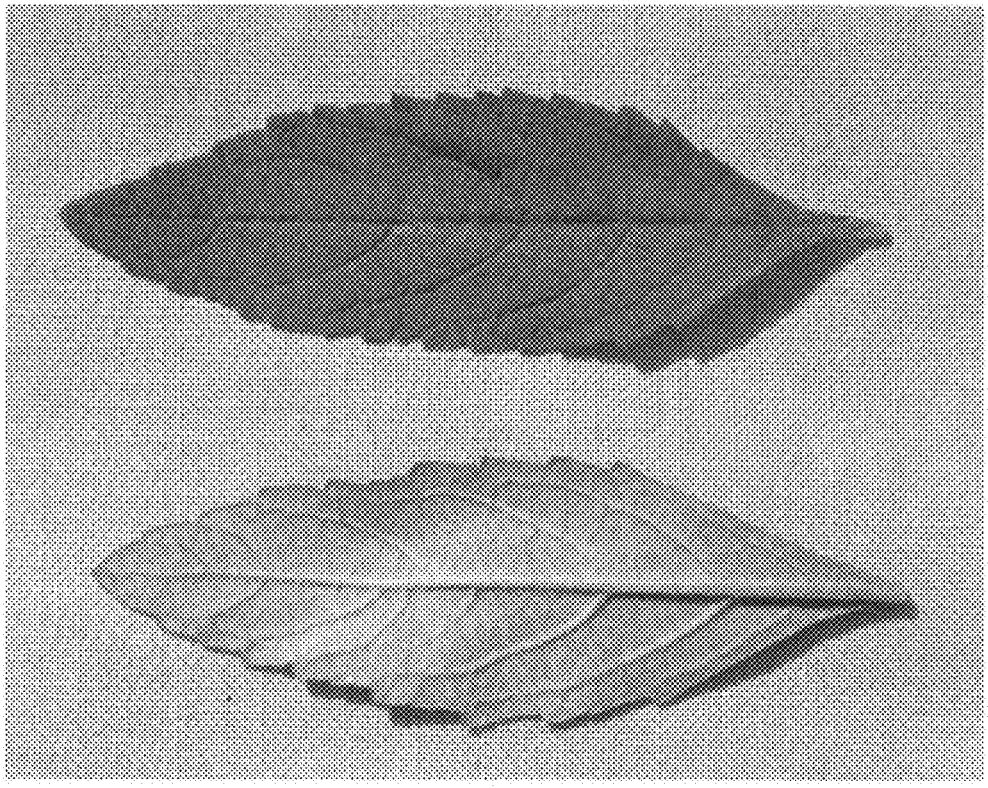
FIG. 3 shows the typical coloration and form of leaves of 'ICE CHIP'. This figure shows the upper (top) and lower (bottom) leaf surface.
Figure 4:
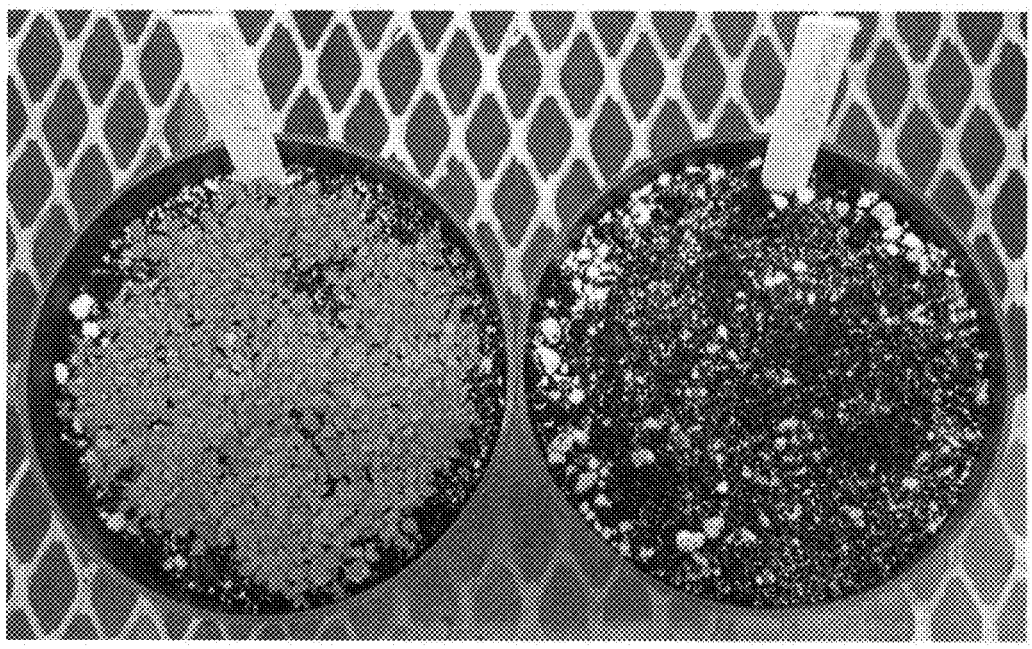
FIG. 4 shows lack of seed germination (right pot) from 'Ice Chip' (5 entire flower panicles crushed and sown) as compared to the high numbers of seedlings derived from only a small subset of seed pods on one flower panicle of commercial variety 'Black Knight' (left pot).

The following is a detailed description of the botanical and ornamental characteristics of the subject butterfly bush 'ICE CHIP'. Color data are based on The Royal Horticultural Society Colour Chart, The Royal Horticultural Society, London, 2007 edition. Where dimensions, sizes, colors and other characteristics are given, it is to be understood that such characteristics are approximations of averages set forth as accurately as practicable.

The descriptions reported herein are from four-year-old specimens grown in field research trials in Jackson Springs, N.C.

Genus: *Buddleja*.

Species: Complex hybrid, including *davidii, globosa*, and *lindleyana*.

Denomination: 'ICE CHIP'.

Commercial classification: Shrub, deciduous.

Common name: Butterfly bush.

Uses: Patio container plant, herbaceous perennial border, or shrub border for residential and commercial landscapes.

Cultural requirements: Full sun exposure, well-drained soil, and moderate moisture.

Parentage: 'ICE CHIP' is a sixth-generation hybrid that resulted from the most recent cross pollination of 'Blue Chip'×NC2002-12. See Table 1 in "Background" for entire pedigree.

Plant description:

*Blooming period*.—June through October.
*Blooming habit*.—Paniculate.
*Vigor*.—Low vigor.
*Plant habit*.—Dwarf, spreading habit.
*Height and spread*.—0.80 m (height) and 1.84 m (width) on four-year-old plants.
*Hardiness*.—To date, hardy to minus 8 degrees Centigrade. Not tested below this temperature. Anticipated adapted from USDA hardiness zones 5-9.
*Propagation*.—Softwood to semi-hardwood cuttings under intermittent mist. Roots typically form in 2-3 weeks.
*Root system*.—Fibrous, spreading.
*Seasonal interest*.—White flowers in spring, summer, and fall on a dwarf shrub with spreading growth habit.
*Disease and pest susceptibility and resistance*.—No particular susceptibility or resistance, except occasionally susceptible to spider mites under very hot and dry conditions.
*Special growing requirements*.—Moderate yearly pruning in late winter or early spring prior to bud break is recommended to encourage more profuse flowering.

Stems:

*Shape*.—Stem cross section is quadrangular.
*Length*.—Average 29.3 cm.
*Color*.—Yellow-green (RHS 145A) on recently formed shoots.
*Diameter*.—2.3 mm at base of new growth.
*Stem surface*.—Pubescent.
*Pubescence*.—Sparse.
*Internode length*.—2.9 cm in the middle of new growth.

Foliage:

*Type*.—Deciduous.
*Leaf arrangement*.—Opposite, decussate.
*Leaf division*.—Simple.
*Leaf shape*.—Elliptic.
*Leaf base*.—Attenuate.
*Leaf apex*.—Acuminate.
*Leaf venation*.—Pinnate.
*Leaf surface* (*abaxial*).—Glaucous.
*Leaf margin*.—Serrulate.
*Leaf attachment*.—Petiolate.
*Petiole dimensions*.—2.6 mm length. 1.0 mm width.
*Petiole shape*.—Sulcate and pubescent.
*Petiole color*.—RHS 145B.
*Leaf color*.—Adaxial side=green (RHS 137B). Abaxial side=grayed-green (RHS 194D).
*Leaf length*.—Average length (5 leaves)=7.4 cm.
*Leaf width*.—Average width (5 leaves)=2.7 cm.
*Foliar fragrance*.—None detectable.

Flowers:

*Inflorescence*.—Loose panicle.
*Flower shape*.—Salverform.
*Petals*.—4 in number.
*Fused or unfused*.—Fused at base, occasional flower showing unfused condition.
*Petal margin*.—Entire.
*Petal apex*.—Rounded lobes, serrulate.
*Petal base*.—Truncate.
*Petal surfaces*.—Glaucous.
*Petal shape*.—Rotund.
*Petal dimensions*.—8.4 mm total length. 5.4 mm width at apex. 1.0 mm at base.
*Petal color*.—Adaxial and abaxial surface (open flower)=white (RHS NN155B). Closed flower prior to opening=white (NN155C).
*Corolla tube color*.—Outside of corolla=greyed-yellow (RHS 161B).
*Corolla throat color*.—Inside of corolla=greyed-yellow (RHS 162A).
*Corolla tube surfaces* (*inner and outer surfaces*).—Pubescent.
*Corolla tube shape*.—Tubular.
*Color of peduncle*.—Green (RHS 138B).
*Peduncle surface*.—Glaucous.
*Peduncle length*.—8.1 cm.
*Peduncle shape*.—Flattened oval in cross section.
*Pedicel dimensions*.—2.4 mm in length and less than 1 mm in diameter.
*Pedicel color*.—Green (RHS 138B).
*Pedicel shape*.—Flattened oval in cross section.
*Pedicel surface*.—Glaucous.
*Flowers persistent or self-cleaning*.—Flowers are persistent.
*Lastingness of the overall inflorescence*.—7-10 days.
*Lastingness of an individual flower*.—3-5 days.
*Dimensions of inflorescence*.—8.1 cm length. 5.4 cm width at base, tapering to 1 mm at tip.
*Quantity of flowers*.—94.8 flowers per panicle (average of 5 panicles).
*Bud apex*.—Rounded lobes, serrulate.
*Bud surface*.—Glaucous.
*Bud shape*.—Elongated, linear balloon.
*Calyx shape*.—Tubular.
*Calyx dimensions*.—2.0 mm in width and 4.0 mm in length.
*Sepals*.—Four in number.
*Sepal shape*.—Lanceolate.
*Sepal apex*.—Acute.
*Sepal margin*.—Entire.
*Sepal surface*.—Glabrous.
*Sepal color*.—Green (RHS 138B).
*Flower fragrance*.—Distinct sweet fragrance.

Reproductive organs:

*Stamens*.—Absent.
*Anther shape*.—Absent.
*Filament size*.—Absent.
*Pollen amount*.—Absent.
*Pistil*.—One in number.

*Pistil dimensions.*—3 mm in length, and less than 1 mm in diameter.

*Stigma color.*—Yellow-green (RHS 144C).

*Ovary.*—Present.

*Ovary position.*—Superior.

*Ovary shape.*—Oval.

*Fertility.*—Low to no seed set in a field setting.

Fruit:

*Type.*—Swollen capsule. Rarely observed.

*Dimensions.*—2.0 mm length (variable) and 1.2 mm diameter (variable).

*Color.*—Yellow-green (RHS 144C) when immature.

Herbarium voucher: A voucher of 'Ice Chip' will be deposited into the Herbarium of NC State University (NCSU) in Raleigh, N.C., USA upon patenting.

The invention claimed is:

1. A new and distinct variety of butterfly bush plant (*Buddleja*) substantially as illustrated and described, characterized by at least one of its dwarf growth, dense and spreading growth habit, white flower color, male sterility and female structures that are essentially sterile.

* * * * *